United States Patent [19]
Landis et al.

[11] Patent Number: 5,608,917
[45] Date of Patent: Mar. 11, 1997

[54] ERGONOMIC HEAD BAND APPARATUS

[75] Inventors: Timothy J. Landis, Loomis; Kyle D. Fields, El Dorado Hills; James P. Dudley, Sacramento; Scott M. Perry, Colfax, all of Calif.

[73] Assignee: OP-D-OP, Inc., Roseville, Calif.

[21] Appl. No.: 614,820

[22] Filed: Mar. 7, 1996

Related U.S. Application Data

[63] Continuation-in-part of Ser. No. 388,671, Feb. 13, 1995, abandoned.

[51] Int. Cl.⁶ .................. A42B 1/22; A42B 3/14
[52] U.S. Cl. .................. 2/418; 2/9; 2/11; 2/183; 2/DIG. 11
[58] Field of Search .................. 2/8, 9, 10, 417, 2/418, 419, 420, 183, DIG. 11, 11

[56] References Cited

U.S. PATENT DOCUMENTS

| | | |
|---|---|---|
| D. 206,191 | 11/1966 | Lawrence . |
| 797,293 | 8/1905 | Lang et al. . |
| 2,187,932 | 1/1940 | Cornell .................. 2/8 |
| 2,194,492 | 3/1940 | Bowers . |
| 2,262,449 | 11/1941 | Buegeleisen . |
| 2,603,784 | 7/1952 | Persons . |
| 2,638,593 | 5/1953 | Eloranta . |
| 2,829,374 | 4/1958 | Malcolm, Jr. . |
| 3,555,562 | 1/1971 | Patton, Jr. . |
| 3,866,244 | 2/1975 | Ruck .................. 2/8 |
| 3,868,727 | 4/1975 | Paschall . |
| 4,117,553 | 10/1978 | Bay . |
| 4,523,808 | 6/1985 | Miller et al. . |
| 4,701,965 | 10/1987 | Landis . |
| 4,850,049 | 7/1989 | Landis et al. . |
| 4,852,186 | 8/1989 | Landis . |
| 4,864,653 | 9/1989 | Landis . |
| 4,888,831 | 12/1989 | Oleson .................. 2/420 |
| 4,964,171 | 10/1990 | Landis . |
| 5,077,836 | 1/1992 | Idoff et al. .................. 2/10 |

*Primary Examiner*—Michael A. Neas
*Attorney, Agent, or Firm*—John P. O'Banion

[57] ABSTRACT

An ergonomic head band which may be comfortably worn for extended periods of time. The head band includes a strap having first and second upwardly curved side arcuate segments, a front arcuate region, and tails which couple together at the back of a wearer's head. Platform regions are provided between the front arcuate region and side arcuate segments. The side arcuate segments comfortably accommodate the ears of a wearer while the head band is worn, while the front arcuate region is positioned adjacent the wearer's head. The platform regions allow face shields or other apparatus to be coupled to the head band.

16 Claims, 3 Drawing Sheets

ERGONOMIC HEAD BAND APPARATUS

CROSS-REFERENCE TO RELATED APPLICATIONS

This application is a continuation-in-part of copending application Ser. No. 08/388,671 filed on Feb. 13, 1995, now abandoned, the disclosure of which is incorporated herein by reference.

BACKGROUND OF THE INVENTION

1. Field of the Invention

This invention pertains generally to head bands and head-worn straps. Particularly, the present invention relates an ergonomic head band which is comfortable to wear for extended periods of time without re-positioning or adjustment, and which is suitable for supporting visors, face shields, and other apparatus from the head band.

2. Description of the Background Art

Head bands or straps are commonly used for supporting visors, bills and shades on a person's head to reduce glare and to prevent sunburn. Head bands are also frequently used in dental, medical and other professions to support face shields, goggles, lights, reflectors, mirrors, magnifying optics, tinted glass or other apparatus from a wearer's head. Conventional head bands typically comprise a plain strap or band of flexible or resilient material, which encircles the wearer's head above the ears and generally across the forehead, with the ends of the band coupled together at the back of the wearer's head. Another common head band configuration employs a pair of resilient, rearwardly disposed tails or arms which partially encircle and tensionally engage the wearer's head. Yet another standard head band comprises a continuous elastic loop which encircles the wearer's head.

A common problem experienced with visors, face shields or other devices supported by a head band is that conventional head bands are uncomfortable to wear, particularly for extended periods of time. The wearers must frequently reposition the head band to minimize discomfort. Also, the problem of discomfort is further acerbated by the fact that physicians, dentists, welders, and other persons who rely on apparatus supported by head bands frequently have both hands occupied in difficult or complex procedures, and cannot free their hands to positionally adjust the head bands to reduce discomfort.

Accordingly, there is a need for an ergonomic head band which is comfortable to wear for extended periods of time, which does not require frequent repositioning by wearers to reduce discomfort, and which may be used to support visors, face shields, and other devices from a wearer's head. The present invention satisfies these needs, as well as others, and generally overcomes the deficiencies found in the background art.

SUMMARY OF THE INVENTION

The present invention pertains to an ergonomic head band which is comfortable to wear for extended periods of time, which does not require frequent repositioning to reduce wearer discomfort, and which is suitable for supporting a variety of devices while worn on a person's head. In general terms, the invention comprises an elongated band or strap with first and second ends or tails, first and second side arcuate segments adjacent the first and second tails, and a forward or front arcuate region between the first and second side arcuate segments. Means for supporting objects from the head band are provided, preferably comprising a first platform region included on the strap between the first side arcuate segment and front arcuate region, and a second platform region included between the second side arcuate segment and front arcuate region.

By way of example and not of limitation, the front arcuate region has a broad, shallow angle of arc and preferably is upwardly curved or bowed. The side arcuate segments preferably have slightly narrower angles of arc than that of the front arcuate region, and also are upwardly curved or bowed. The platform regions preferably comprise wide areas with flat outer surfaces on the band which are positioned between the front arcuate region and side arcuate segments. Attachment means may be included on the platform regions for supporting face shields, visors or other head-worn devices. The platform regions define a kink or bend in the overall shape of the elongated strap such that the side arcuate segments are upwardly displaced from the front arcuate region. Cushioning means and/or perspiration absorbing means may be included on inner surfaces of the side arcuate segments and/or front arcuate region to increase wearer comfort. Ventilation holes may be provided in the side arcuate segments and/or front arcuate region to further increase wearer comfort. The tails or ends preferably are straight in configuration, and generally include one of a variety of standard means for coupling the tails together so that the head band encircles the wearer's head.

The invention is worn on a wearer's head such that the side arcuate segments are positioned over the wearer's ears, the front or forward arcuate region is positioned adjacent the wearer's forehead, and the tails are coupled together at the back of the wearer's head. Thus worn, the platform regions are generally adjacent the sides of the wearer's head forward of the wearer's ears, to allow pivotal or articulating attachment of face shields, visors, or like items to the head band.

An object of the invention is to provide an ergonomic head band which is comfortable to wear for extended periods of time.

Another object of the invention is to provide an ergonomic head band which does not require frequent repositioning to maintain wearer comfort.

Another object of the invention is to provide an ergonomic head band which is suitable for attachment or supporting of face shields, visors and other head-worn devices.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Figure 1:
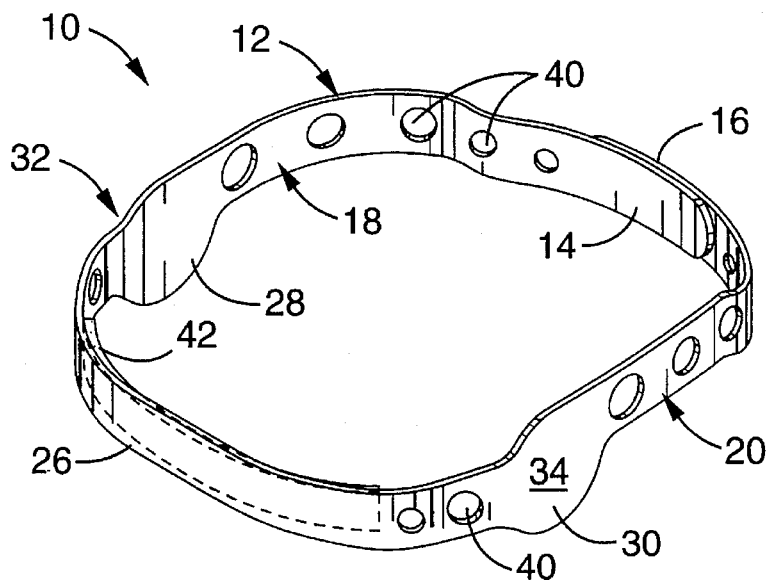
FIG. 1 is a perspective view of an ergonomic head band in accordance with the present invention.
Figure 2:
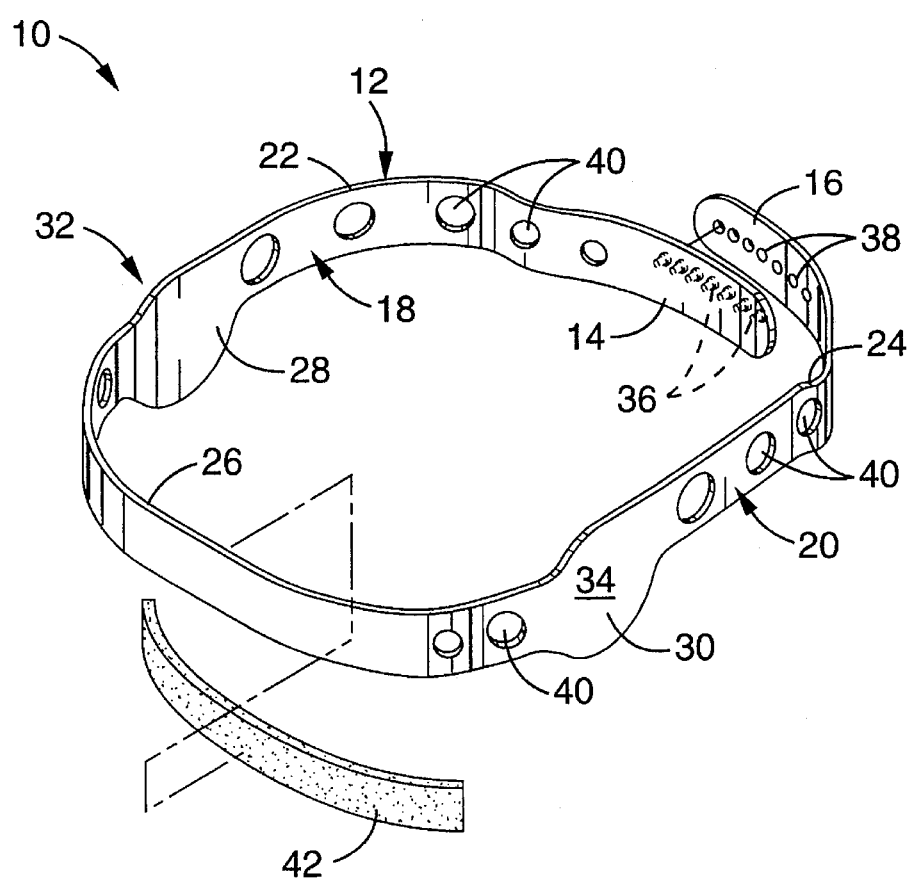
FIG. 2 is an exploded view of the ergonomic head band of FIG. 1.
Figure 3:
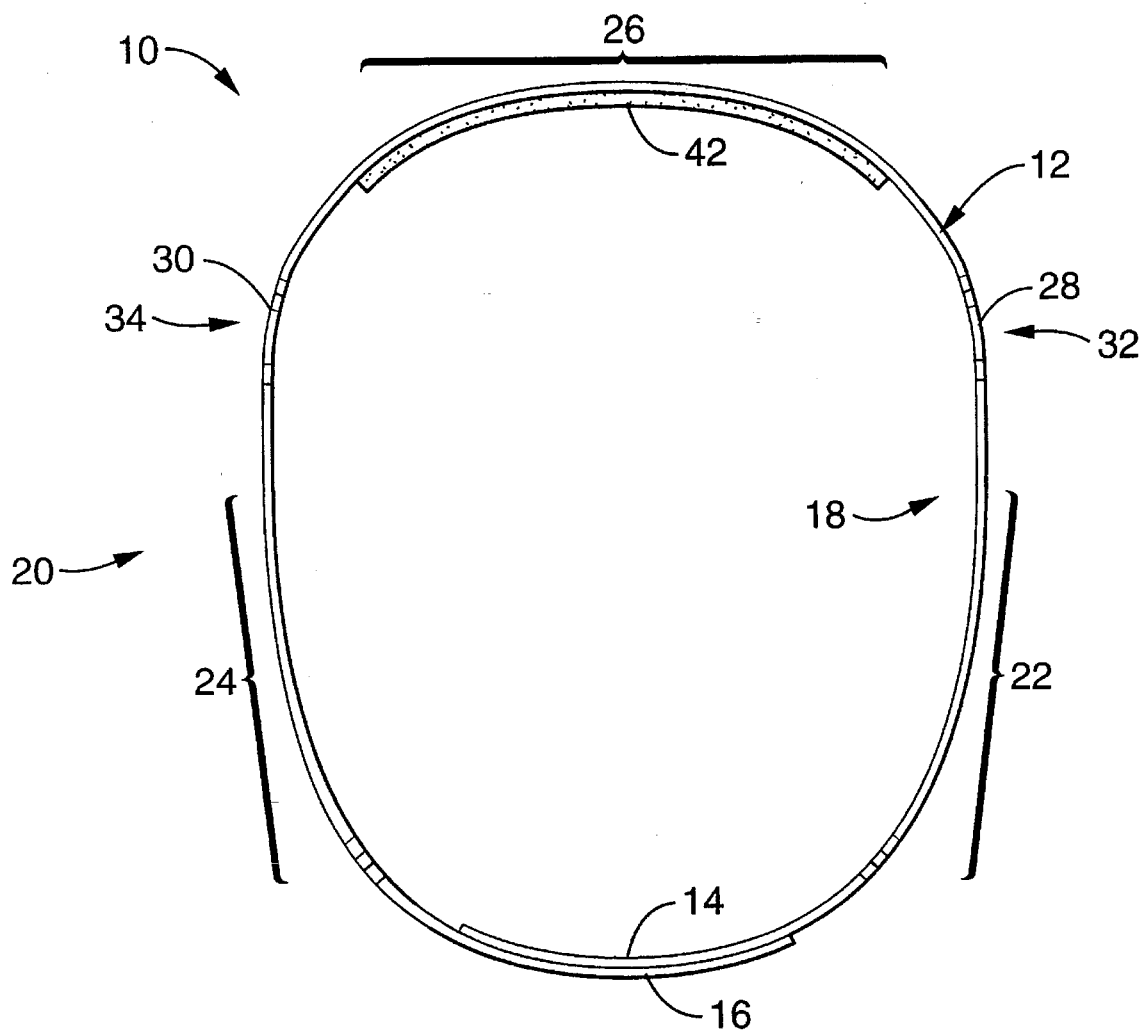
FIG. 3 is a top plan view of the head band of FIG. 1.

Referring more specifically to the drawings, for illustrative purposes the present invention is embodied in the apparatus generally shown in FIG. 1 through FIG. 4. It will be appreciated that the apparatus may vary as to configuration and as to details of the parts without departing from the basic concepts as disclosed herein.

Referring now to FIG. 1 through FIG. 4, an ergonomic head band apparatus 10 in accordance with the present invention is generally shown. The head band apparatus 10 includes an elongated strap 12 having first and second ends or tails 14, 16 respectively. Strap 12 is preferably of flat configuration, and includes an inner, head-facing surface 18 and an outer surface 20. However, in the embodiment of the invention shown in FIG. 1 through FIG. 4, head band 10 can be worn such that inner and outer surfaces 18, 20 are interchangeable. Strap 12 is preferably fabricated from a flexible or resilient material such as a polyethylene sheet of suitable thickness or other light weight, flexible polymeric material. Strap 12 may also be made from a woven fabric material or leather.

Head band 10 includes first and second side arcuate regions 22, 24, with first side arcuate region 22 located adjacent first tail 14, and second side arcuate region 24 located adjacent second tail 16. First and second side arcuate regions 22, 24 are preferably convexly curved or bowed in an upward direction, and are generally structured and configured to be comfortably positioned above the ears of a wearer while head band 10 is positioned on a wearer's head, as discussed below. First side arcuate segment 22 has an angle of arc which is generally equal to the angle of arc of second side arcuate region 24.

A forward or front arcuate region or domain 26 is provided on head band 10, with front arcuate region 26 positioned generally between first and second side arcuate regions 22, 24. Front arcuate region 26 is preferably convexly curved or bowed in an upward direction as shown to comfortably accommodate a wearer's forehead. Front arcuate region 26 may alternatively be concavely curved or bowed in a downward orientation. Front arcuate region 26 preferably has a generally broad, shallow angle of arc, with the angle of arc of side arcuate segments 22, 24 being generally narrower than the angle of arc of front arcuate region 26, as can be seen most clearly by reference to FIG. 4.

Preferably, first and second platforms or platform regions 28, 30 are included on head band 10 to provide means for supporting various devices. First platform 28 is positioned between first side arcuate segment 22 and front arcuate region 26, and second platform 30 is positioned between second side arcuate segment 24 and front arcuate region 26. Platforms 28, 30 are provided to accommodate various attachment means (not shown) for coupling various items of devices to head band 10. The present invention is particularly suitable for supporting visors, bills, shades, face shields, eye shields, lights, reflectors, mirrors, magnifying optics, tinted glass or other apparatus directly from head band 10. The attachment or coupling means which may be used with the invention include articulating or pivoting hinge assemblies for positionally adjustable face shields and/or visors, VELCRO® type hook and loop fasteners, snap fastener arrangements, adhesives or other standard coupling means which may be used to attach the aforementioned devices to head band 10. The attachment means are mounted onto platforms 28, 30. First and second platforms 28, 30 each preferably have generally flat, outward facing mounting surfaces 32, 34 respectively, to facilitate the use of various coupling or attachment means with the invention. Platforms 28, 30 are preferably positioned on head band 10 such that platforms 28, 30 will be positioned on the sides of a wearer's head and forward of the wearer's ears while head band 10 is worn.

Means for coupling first tail 14 and second tail 16 together are also included with the invention. The coupling means preferably comprises a plurality of studs or protrusions 36 included on first tail 14, and a plurality of corresponding or matching holes 38 included on second tail 16, with holes 38 and studs 36 structured and configured to reversibly snap fit in a conventional manner. Alternatively, studs 36' may be included on second tail 16 while holes 38 are located on first tail 14. Studs 36 and holes 38 further serve as means for adjusting the circumference of head band 10 while head band 10 is worn on a person's head by selectively engaging particular studs 36 with particular holes 38 in a standard fashion. Preferably, a numeric positioning scheme (not shown) is utilized in conjunction with holes 38 and studs 36 to indicate to the user the particular circumferential adjustment which will be provided by snap fitting particular studs 36 within particular holes 38. For example, a numeric indication of standard hat size, head circumference, or other numeric size indicator may be included adjacent each individual stud 36 and a corresponding individual hole 38.

The means for coupling first and second tails 14, 16 together may alternatively comprise a buckle fastener, VELCRO® type hook and loop fasteners, button arrangements, or other common coupling means which may be used to fasten first and second tails 14, 16 together such that head band 10 may be worn on a wearer's head.

A plurality of openings or holes 40 may be provided along strap 12 to serve as ventilation means and to reduce perspiration by a wearer which may cause discomfort. Cushioning means, such as pad 42 may be included on inner surface 18 of strap 12 to further increase wearer comfort. While a pad 42 is shown only on front arcuate region 26, additional pads may be included on other portions of strap 12. Similarly, the number and location of ventilation holes 40 may be varied as required for particular applications of the invention.

Figure 4:
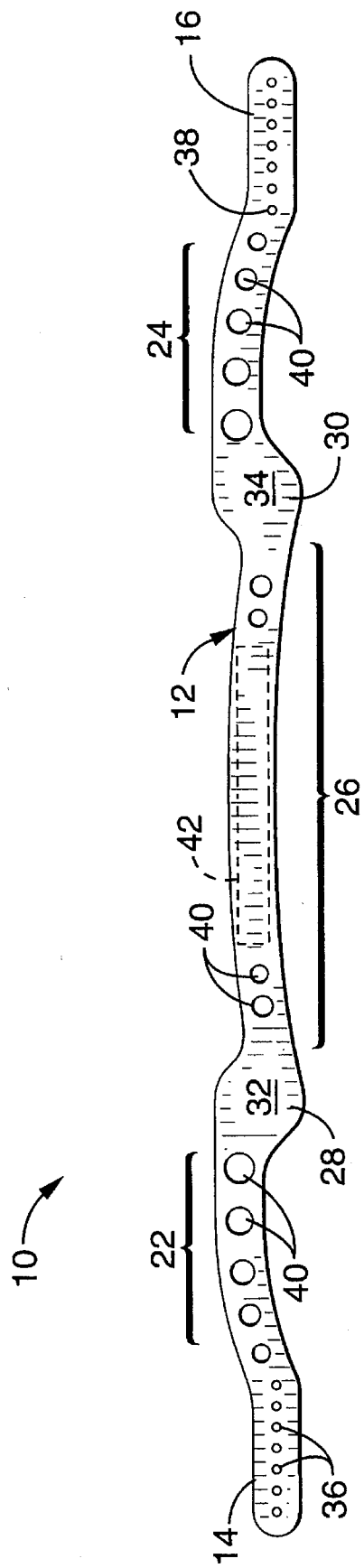
FIG. 4 is a side view of the head band of FIG. 1 shown fully extended.

Referring more particularly to FIG. 4, it can be seen that platforms 28, 30 generally define kinks or bends in strap 12 so that strap 12 does not have a completely linear structure and configuration in standard, background art head band devices. Instead, first and second side arcuate regions 22, 24 are upwardly displaced generally from front arcuate region 26. The curved or arcuate shape of side arcuate regions result in first and second tails 14, 16 be generally co-linear with the central portion of front arcuate region 26.

The head band 10 comprising the present invention is utilized by encircling strap 12 about the wearer's head and coupling first and second tails 14, 16 together in a conventional manner, with studs 36 and holes 38 selectively interfitted to correspond generally to the circumference of the wearer's head. Side arcuate regions 22, 24 are positioned above and adjacent to the wearer's ears, and front arcuate region is positioned adjacent the wearer's forehead. The slight upward displacement of side arcuate segments 22, 24, together with the upwardly curved arcuate nature of side arcuate segments 22, 24, allow the head band to be comfortably worn over the wearer's ears. The broad, shallow curve of the front arcuate region 26 serves to comfortably accommodate the wearer's forehead.

As mentioned above, strap 12 is preferably fabricated from a flexible or resilient polymeric sheet material such as polyethylene. However, it is contemplated that different portions of strap 12 be made from different types of materials. For example, side arcuate segments 22, 24 and front arcuate segment 26 may be made of generally soft, pliable material to maximize wearer comfort, while platforms 28, 30 are fabricated from a more rigid, durable material to facilitate support of a face shield or other device thereupon. Several specific polymeric materials suitable for fabrication of strap 12 or portions thereof are discussed in U.S. Pat. application Ser. No. 08/396,411.

Accordingly, it will be seen that this invention provides an ergonomic head band which is comfortable to wear for extended periods of time and which is suitable for supporting face shields, visors, or other apparatus. Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. A head band apparatus, comprising:
(a) an elongated strap, said strap having first and second tails;
(b) said strap including first and second side arcuate segments, said first side arcuate segment adjacent said first tail, said second side arcuate segment adjacent said second tail;
(c) said strap including a front arcuate region, said front arcuate region positioned between said first and second side arcuate segments, said front arcuate region bowed in an upward direction; and
(d) means for coupling said first tail to said second tail.

2. An apparatus as recited in claim 1, further comprising means for supporting objects from said head band.

3. An apparatus as recited in claim 2, wherein said supporting means comprises first and second platforms, said first platform positioned between said first side arcuate segment and said front arcuate region, said second platform positioned between said second side arcuate segment and said front arcuate region.

4. An apparatus as recited in claim 1, wherein each said side arcuate segment is bowed in an upward direction.

5. An apparatus as recited in claim 1, wherein said first side arcuate segment has an angle of arc equal to an angle of arc of said second side arcuate segment, said angle of arc of said first and second side arcuate segments being narrower than an angle of arc of said front arcuate region.

6. An apparatus as recited in claim 1, wherein said coupling means further comprises means for adjusting the circumference of said strap.

7. An apparatus as recited in claim 1, wherein said first and second side arcuate segments are upwardly displaced relative to said front arcuate region and said first and second tails.

8. A head band apparatus, comprising:
(a) an elongated strap, said strap having first and second tails;
(b) said strap including first and second side arcuate segments, said first side arcuate segment adjacent said first tail, said second side arcuate segment adjacent said second tail;
(c) said strap including a front arcuate region, said front arcuate region positioned between said first and second side arcuate segments, said front arcuate region bowed in an upward direction;
(d) said strap including first and second platforms said first platform located between said first side arcuate segment and said from arcuate region, said second platform located between said second side arcuate segment and said front arcuate region; and
(e) means for coupling said first tail to said second tail.

9. An apparatus as recited in claim 8, wherein each said side arcuate segment is bowed in an upward direction.

10. An apparatus as recited in claim 9, wherein said first side arcuate segment has an angle of arc equal to an angle of arc of said second side arcuate segment, said angle of arc of said first and second side arcuate segments being narrower than an angle of arc of said front arcuate region.

11. An apparatus as recited in claim 8, wherein said coupling means further comprises means for adjusting the circumference of said strap.

12. An apparatus as recited in claim 8, wherein said first and second side arcuate segments are upwardly displaced relative to said front arcuate region and said first and second tails.

13. A head band apparatus, comprising:
(a) an elongated strap, said strap having first and second tails;
(b) said strap including first and second side arcuate segments, said first side arcuate segment adjacent said first tail, said second side arcuate segment adjacent said second tail, said first and second side arcuate segments each bowed in an upward direction;
(c) said strap including a front arcuate region, said front arcuate region positioned between said first and second side arcuate segments, said front arcuate region bowed in an upward direction;
(d) said strap including first and second platforms, said platforms each having a flat outer mounting surface, said first platform located between said first side arcuate segment and said front arcuate region, said second platform located between said second side arcuate segment and said front arcuate region; and
(e) means for coupling said first tail to said second tail.

14. An apparatus as recited in claim 13, wherein said coupling means further comprises means for adjusting the circumference of said strap.

15. An apparatus as recited in claim 13, wherein said first side arcuate segment has an angle of arc equal to an angle of arc of said second side arcuate segment, said angle of arc of said first and second side arcuate segments being narrower than an angle of arc of said from arcuate region.

16. An apparatus as recited in claim 13, wherein said first and second side arcuate segments are upwardly displaced relative to said front arcuate region and said first and second tails.

* * * * *